(12) United States Patent
Hedman et al.

(10) Patent No.: US 9,492,592 B2
(45) Date of Patent: *Nov. 15, 2016

(54) CROSSLINKER ENHANCED REPAIR OF KNEE MENISCUS

(71) Applicant: Orthopeutics, L.P., Lexington, KY (US)

(72) Inventors: Thomas P. Hedman, Lexington, KY (US); Pawel Slusarewicz, Lexington, KY (US)

(73) Assignee: Orthopeutics, L. P., Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/685,539

(22) Filed: Apr. 13, 2015

(65) Prior Publication Data

US 2015/0217025 A1    Aug. 6, 2015

Related U.S. Application Data

(60) Division of application No. 13/700,091, filed as application No. PCT/US2011/038155 on May 26, 2011, now abandoned, and a continuation-in-part of application No. 12/715,737, filed on Mar. 2, 2010, now Pat. No. 8,211,938, which is a division of application No. 11/712,684, filed on Feb. 28, 2007, now Pat. No. 8,022,101, said application No. PCT/US2011/038155 is a continuation-in-part of application No. 11/975,072, filed on Oct. 17, 2007, now Pat. No. 8,119,599, which is a continuation-in-part of application No. 11/726,790, filed on Mar. 22, 2007, now abandoned.

(60) Provisional application No. 61/348,977, filed on May 27, 2010.

(51) Int. Cl.

| A61F 9/00 | (2006.01) |
| A61F 2/00 | (2006.01) |
| A61L 27/54 | (2006.01) |
| A61L 31/04 | (2006.01) |
| A61L 31/14 | (2006.01) |
| A61F 2/30 | (2006.01) |
| A61L 27/18 | (2006.01) |
| A61L 27/34 | (2006.01) |
| A61L 27/50 | (2006.01) |
| A61L 27/58 | (2006.01) |
| A61F 2/38 | (2006.01) |

(52) U.S. Cl.
CPC ............ *A61L 27/54* (2013.01); *A61F 2/30756* (2013.01); *A61L 27/18* (2013.01); *A61L 27/34* (2013.01); *A61L 27/505* (2013.01); *A61L 27/58* (2013.01); *A61L 31/043* (2013.01); *A61L 31/14* (2013.01); *A61F 2/0063* (2013.01); *A61F 2/3872* (2013.01); *A61F 2250/0067* (2013.01); *A61L 2300/412* (2013.01); *A61L 2430/06* (2013.01)

(58) Field of Classification Search
None
See application file for complete search history.

(56) References Cited

U.S. PATENT DOCUMENTS

| 6,812,211 | B2 * | 11/2004 | Slivka et al. ............... 424/94.4 |
| 9,084,772 | B2 | 7/2015 | Hedman |
| 9,101,602 | B2 | 8/2015 | Hedman |
| 9,192,507 | B2 | 11/2015 | Hedman et al. |
| 2003/0036797 | A1 * | 2/2003 | Malaviya et al. ......... 623/14.12 |
| 2003/0082116 | A1 * | 5/2003 | Badejo et al. ................. 424/58 |
| 2006/0069011 | A1 * | 3/2006 | Kusanagi et al. ................ 514/2 |
| 2009/0177228 | A1 * | 7/2009 | Aspenberg et al. .......... 606/228 |
| 2009/0311338 | A1 * | 12/2009 | Pathak et al. ................ 424/529 |

FOREIGN PATENT DOCUMENTS

DE    4412190 A1    10/1995

* cited by examiner

*Primary Examiner* — Thomas J Visone
(74) *Attorney, Agent, or Firm* — Berliner & Associates

(57) ABSTRACT

A method of treating a tear in a knee meniscus of a patient. The method includes exposing the torn knee meniscus to a protein crosslinker during surgery to repair the tear. Also provided is a fixation device for the surgical repair of tears of the meniscus of the knee, where the device contains one or more protein crosslinking reagents.

24 Claims, 1 Drawing Sheet

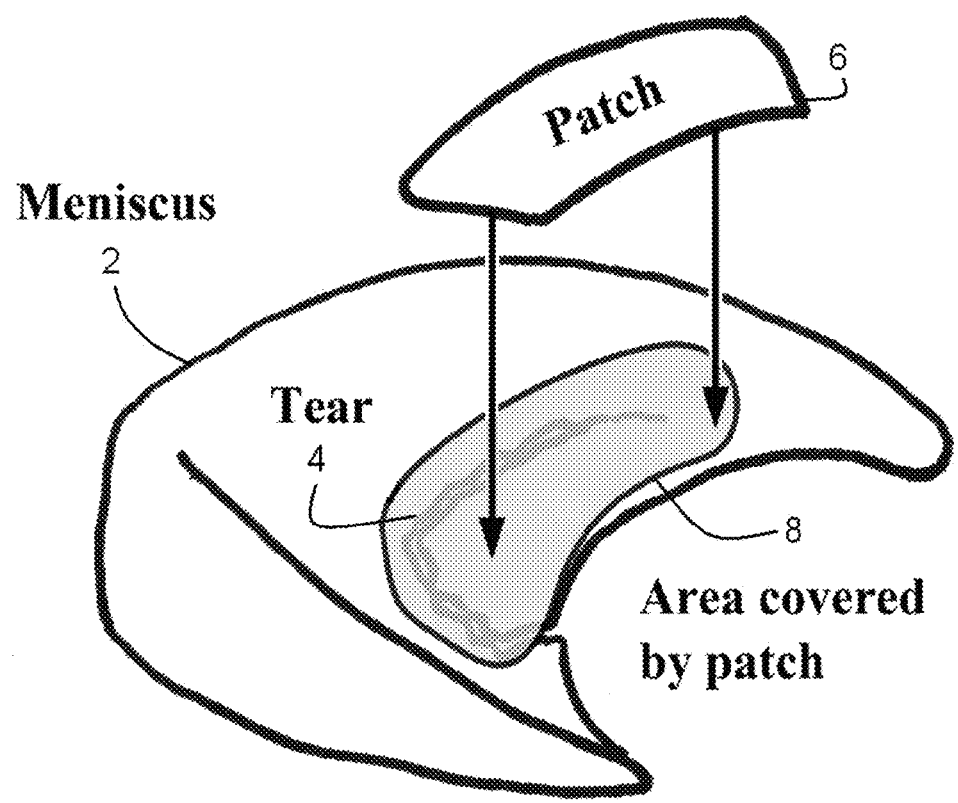

CROSSLINKER ENHANCED REPAIR OF KNEE MENISCUS

CROSS-REFERENCE TO RELATED APPLICATIONS

This application is a divisional application of application Ser. No. 13/700,091, which is the National Stage of International Application PCT/US2011/038,155, filed on May 26, 2011, which is a continuation-in-part of application Ser. No. 12/715,737, filed on Mar. 2, 2010, which is a divisional of application Ser. No. 11/712,684, filed Feb. 28, 2007. International Application PCT/US2011/038,155, filed on May 26, 2011, is also a continuation-in-part of application Ser. No. 11/975,072, filed Oct. 17, 2007, which is a continuation-in-part of application Ser. No. 11/726,790, filed Mar. 22, 2007. International Application PCT/US2011/038, 155, filed on May 26, 2011, claims the benefit of Provisional Patent Application No. 61/348,977, filed on May 27, 2010. All of the foregoing applications are incorporated by reference herein.

BACKGROUND

1. Field of the Invention

The present invention relates to protein crosslinking reagents for the surgical repair of torn knee menisci in humans or similar connective tissue structures in animals such as the stifle joint meniscus in equines.

2. Related Art

The menisci of the knee are a pair of crescent-shaped fibrocartilaginous structures attached to the planar apical surface of the tibia. They contact the outer region of the femoral articular cartilage surface and as such play an important role in both load transmission and in maintaining the stability of the joint [1-6].

While 65-75% of the mass of the menisci consists of water, the remaining constituents are primarily proteins with the most common (75%) being type I collagen [7], and damage to this tissue is one of the most common causes of knee injury and results in surgery to some 850,000 patients per year in the US [8]. Symptoms of meniscal tears are primarily localized pain and swelling but, in cases where fragments of the damaged meniscus lodge between the articulating surfaces of the joint, catching sensations and (in the worst case) locking of the joint can occur.

The first line of treatment for meniscal tears are non-surgical, e.g. rest, icing, physical therapy and/or non-steroidal anti-inflammatory drug (NSAID) treatment. Surgery is indicated for patients who do not respond to physical therapy, who cannot or are unable to sacrifice the time required for potentially unsuccessful therapy and for those with locked joints.

Surgery is most commonly, but not exclusively, conducted arthroscopically to minimize further damage to the joint and to decrease patient recovery times. Damage to the outer periphery of either meniscus heals more readily than that to the inner portions [9,10], due to the lack of vasculature in the inner portion of the meniscus [11]. For this reason, tears of the inner meniscus are usually excised in a procedure known as a partial meniscectomy. In the remaining cases, tears are repaired using either suture or a variety of commercially available, fixing devices such as arrows, darts and tacks [12-14] in order to facilitate healing of the tear. These devices are generally constructed using biodegradable polymers such as polylactic or polyglycolic acid so that no subsequent surgery is required for their removal.

Although the latter class of devices provides temporary support to the tissue as it heals, they are in general not as strong as sutures [12,13]. However, because their use results in substantially reduced operating times and risk of complications to the patient, they are increasingly gaining favor [12,13].

While the above represents the most common approaches to the treatment of meniscal tears, other therapeutic modalities for meniscal repair can be used or are being explored experimentally. These include: stem cell therapy [15,16]; trephination from the vascular to avascular region to facility greater nutrient flow and promote in-growth of vasculature [17-19]; micro-fracture of the intercondylar notch which may release cytokines or autologous stem cells to aid in the repair process [20]; thermal welding of the tear [21]; enhancement of fibroblast proliferation using RF radiation [22,23]; use of fibrin clots to both provide stimuli for both chemotaxis and proliferation of regenerative cells [24-26], sometimes in conjunction with laser soldering [27]; meniscal or synovial rasping to promote healing via the release of growth factors from the tissue [28-31]; and synovial flap grafting at the repair site to provide vasculature [32].

In addition meniscal replacement using both artificial implants and allografts is becoming a treatment option in the case of severe tears where meniscectomy is the only other treatment option [33-40]. In this respect, the possibility of stabilizing allografts and artificial implants against biodegradation using ex vivo protein crosslinking has been explored [41-44]. The inventors are, however, unaware of any prior art with regard to crosslinking of the native meniscus in situ.

SUMMARY

In one aspect, a method of treating a tear in a knee meniscus of a patient in need of such treatment is provided. The method includes exposing the torn knee meniscus to a protein crosslinker (an agent that crosslinks protein) during surgery to repair the tear. In particular embodiments, exposing includes: a) injecting the crosslinker into a knee joint capsule containing the torn knee meniscus; b) injecting the crosslinker into or onto the torn knee meniscus; or c) contacting the torn knee meniscus with a delivery device comprising the crosslinker; or d) any combination thereof. The crosslinker is a compound or substance that can crosslink proteins. The delivery device in any embodiment can include a patch or fixation device comprising the crosslinker. The fixation device may be an arrow, dart, tack or suture.

A patch or fixation device may be biodegradable or non-biodegradable, and may comprise a basic salt, which may be an inorganic or organic basic salt. In embodiments with a patch, the patch may be porous, and may have crosslinker embedded in the pores of the patch. A crosslinker in a patch may be adhered to one side of the patch as part of a semi-solid formulation.

The patch or fixation device may in addition be coated with one or more layers of crosslinker-containing biodegradable polymer. When more than one layer is present, each layer may contain a basic salt, and may contain the same or different basic salt as another layer. In addition, each layer may contain the same or different crosslinker as another layer. In some embodiments, the crosslinker varies from layer to layer.

The patch may be affixed to the meniscus with a biocompatible adhesive. In addition, the patch may be affixed to the meniscus by an associated fixation device such as an arrow, dart, tack or suture. The associated fixation device may itself include a crosslinker, which may be the same or different crosslinker as that in the patch.

In some embodiments, the torn knee meniscus is treated without contracting collagen fibers in the torn knee meniscus by heating.

In another aspect, a delivery device for contacting the knee meniscus is provided. The delivery device comprises a protein crosslinker.

BRIEF DESCRIPTION OF THE DRAWINGS

For a more complete understanding of the present invention, reference is now made to the following descriptions taken in conjunction with the accompanying drawings, in which:

FIG. 1 is a drawing depicting a stylized human knee meniscus with a "parrot beak" type tear.

DETAILED DESCRIPTION

One aspect relates to various biodegradable fixation devices that contain one or more protein crosslinking reagents for the surgical repair of tears of the meniscus of the knee in humans or similar connective tissue structures in animals such as the stifle joint meniscus in equines. Also described are associated methods for repair of tears of the knee meniscus in humans or similar connective tissue structures in animals such as the stifle joint meniscus in equines.

The devices can take various forms including, but not limited to, sutures, tacks, arrows and darts. These devices can be produced using any biodegradable and biocompatible polymer or mixtures of polymers such as, but not limited to, polylactic acid or poly glycolic acid. One or more crosslinking agents may be incorporated into the device. Additionally, the crosslinker can be incorporated into a biodegradable patch which is overlain onto the damaged area of the meniscus during surgery. Alternatively this patch could be made of a non-degradable material and removed at a time following surgery once sufficient crosslinker has been released to facilitate tissue repair.

Following surgery, these reagents are slowly released from the device as it degrades and thereby enter into, and react with, the tissue to form covalent crosslink bonds. These bonds serve to both strengthen the tissue against further and/or future tearing and also increase the permeability of the tissue to nutrients from the blood supply, thereby enhancing the natural healing process. In addition, the increase in tissue permeability conferred by the crosslinking will increase the proportion of meniscal tear patients who can be treated surgically since healing using current methods can only occur in regions with sufficient vascular nutrient supply.

Another aspect relates to the treatment of meniscal tears during surgery with protein crosslinking reagents to modify the mechanical properties and permeability of the meniscal tissue in order to reduce the possibility of further tearing, increase the strength of the tissue and enhance the natural repair process.

Crosslinking of tissue is used extensively to modulate both the mechanical properties and chemical stability of collagenous tissues [45-52]. Historically, crosslinking has been conducted ex vivo to modulate the mechanics and stability of tissue implants, and has been considered with respect to producing allografts for meniscal implant [41], but was not directed at treatment of native meniscal tissues in vivo and in situ, in the tissues original and natural position. Approaches aimed at injection of crosslinkers into native, unmodified tissues in vivo and in situ are also being developed by the inventors (U.S. Pat. No. 7,435,722, and U.S. patent application Ser. No. 10/230,671, both incorporated by reference herein) and others [53] for treatment of the spinal disc.

Use of crosslinking agents and their subsequent reaction with the tissue of the torn meniscus would provide two possible benefits when used in conjunction with current technologies. Firstly, the crosslinker will confer increased tear resistance to the tissue and reduce the possibility of further propagation of the tear as it heals (U.S. application Ser. No. 11/712,684, incorporated by reference herein). This would in turn ameliorate the main disadvantage of fixation devices compared to sutures while maintaining their benefits. If the crosslinker delivery-fixation device is a suture or another device capable of tissue fixation, the crosslinker delivery will further augment the tear resistance of the repair. Secondly, crosslinking has been shown to increase the permeability of collagenous tissues [41,54,55] and thus may increase the permeability of the meniscus. It has been shown that the avascular portions of the meniscus (which do not heal well, if at all, in vivo) are capable of healing in vitro when supplied with sufficient nutrients [11]. Thus the resulting increased supply of nutrients and oxygen to the avascular tissue may both increase the success of the procedure for deeper tears as well as increase the depth at which a tear is considered as a candidate for repair versus meniscectomy.

Particular embodiments combine the beneficial properties of protein crosslinking to improve upon currently used surgical techniques for meniscal repair.

In some embodiments, a torn knee meniscus is treated without contracting collagen fibers in the torn knee meniscus by heating. Heat denaturation of collagenous tissues degrades the tissue by disruption of native crosslinks and tissue structure. The device and methods of exposing the meniscus tissues to the crosslinker may be applied to non-heated, unmodified, native tissues. Thus, the device and methods may be applied without heating, contracting or denaturing the native tissue, or any combination thereof. The native tissue crosslinks are thus augmented or increased by number by exposure to the crosslinker. In some embodiments, the in situ crosslinking method and/or devices may be applied to previously implanted non-native tissue implants or meniscus replacement materials that have not been denatured and/or shrunken by heating.

In some embodiments, the meniscal tissue is pre-treated prior to, or instead of repair by direct injection of crosslinking solution into the capsule of the knee joint or onto or into the damaged tissue itself prior to repair of the tissue. This treatment strengthens the tissue, increases tear resistance, and, in addition, allows for the surgical repair of some tears that will not normally be candidates for repair surgery (due to their inability to heal because of their distance from the blood supply) by increasing the permeability of the tissue. Following injection, the crosslinker diffuses into, and crosslinks, the meniscal tissue, strengthening and increasing tear resistance of the tissue, while also improving the ability of nutrients from the outer vascular regions to diffuse into the inner regions to promote natural healing over a larger area of the meniscus.

In some embodiments, the crosslinker is incorporated into the fixation device itself. Thus, the crosslinker is then released into the tissue in a sustained manner following surgery as the fixation device degrades providing the benefits in physical properties and permeability described above.

Solid or liquid crosslinker may be incorporated into the device by addition to the molten polymer prior to casting, molding or spinning. Alternatively the crosslinker may be co-solubilized with the polymer in a suitable solvent (for example, acetone) and then incorporated into the device by removal of the solvent by evaporation or by precipitation (for example, by the addition of ethanol) of the polymer as described previously [56,57]. The crosslinker and polymer may also be solubilized separately and mixed prior to precipitation in either the same solvent or different (miscible) solvents. Also, the solid crosslinker may also be mixed into the polymer gum formed by precipitation of solubilised polymer and prior to molding. The rate of crosslinker release can be controlled by varying the amount or concentration of the crosslinker incorporated into the device as well as by selecting polymers or other materials with differing in vivo degradation rates.

Alternatively the crosslinker may be co-solubilized with the polymer in a suitable solvent, solubilized separately in the same solvent and then mixed, or solubilized separately in different miscible solvents and then mixed, and a preformed fixation device immersed in this solution. Following removal of the fixation device and evaporation of the solvent, a fixation device containing an outer layer of biodegradable plastic-embedded crosslinker will be produced. The polymer in the outer layer may be different to that of the underlying device both in chain length and/or composition and may be varied, for example, in order to provide different release rates of crosslinker as needed. Additionally, the rate, duration and extent of crosslinker release can be controlled by varying the amount or concentration of the crosslinker incorporated into solvent solution (and therefore the outer layer of the device) as well as by sequential dipping/drying of the fixation device into the crosslinker/polymer/solvent mixture to produce different thicknesses of crosslinker-containing polymer at the surface of the device. Additionally, several crosslinker impregnated outer layers may be used with varying crosslinker amount or concentration and polymer compositions such that the rate of release of crosslinker can be varied as desired. For instance, an initial high rate of crosslinker release can be followed by a low rate of crosslinker release for an extended length of time.

It has been previously shown that many crosslinking reagents act less efficiently at low pH [58]. In addition, some biodegradable polymers degrade to form acidic compounds (for example polylactic acid and polyglycolic acid). In fact, tissue acidification during polymer breakdown has been a concern previously and incorporation of basic inorganic salts into the polymer matrix has been shown to be effective in maintaining an elevated pH [59].

In some embodiments in cases where low-pH sensitive crosslinkers (for example, genipin, methylglyoxal) are used in conjunction with polymers that degrade to form acidic compounds (for example, polylactic or polyglycolic acids), basic salts are also incorporated as solid suspensions into the polymer matrix. Such salts could be inorganic (for example, but not limited to, calcium carbonate, calcium hydroxyapatite or sodium bicarbonate) or organic (for example, but not limited to, 2-Amino-2-hydroxymethyl-propane-1,3-diol (Tris) or 4-(2-hydroxyethyl)-1-piperazineethanesulfonic acid (HEPES).

In some embodiments, the crosslinker is impregnated by one of the methods described above into a flat, biodegradable polymer patch. The patch could contain pH conditioning agents and multiple layers of crosslinking agents as described above. The patch (which could be rolled up and inserted via a catheter) is laid over the repaired tissue such that crosslinker is delivered to the meniscus as the patch dissolves and while the patch offers some physical protection to the damaged meniscal tissue as it heals. The surface of the patch opposite to the meniscus additionally provides a smooth bearing surface to the articular cartilage of the femur. In addition the patch may be attached to the tissue using fixation devices such as, but not limited to, arrows, darts, tacks or suture. These fixation devices may or may not contain additional (including different) crosslinking agent. The patch may also be attached using a suitable biocompatible adhesive. Non-limiting examples of suitable adhesives would be poly(glycerol-co-sebacate acrylate) [60], oleic methyl esters [61] or alkyl ester cyanoacrylates [62].

In some embodiments, the material of the patch consists of a non-absorbable polymer. The patch is placed onto the meniscus during the arthroscopic procedure and can be removed at a subsequent time. Alternatively, the patch may be designed to remain inside the knee as a permanent implant to supplement the mechanical function of the meniscus. The patch may be attached to the meniscus as stated above. Possible, non-limiting, polymers include polyvinylacetate, polyvinylchloride, polypropylene, polyetheretherketone (PEEK), polysulfone, polyethersulfone, polytetrafluoroethylene, polyethylene, polyurethane, polyetherimide and polycarbonate. The non-absorbable patch is either coated or impregnated with crosslinker. The material of the patch could be porous so that the crosslinker or combination of crosslinkers is imbedded within the pores, or non-porous and coated with crosslinker. In the case of a porous patch, the size and the tortuosity of the pores can be varied in order to control the release rate and duration of release of the imbedded crosslinker(s). The crosslinker could be in solid form, in solution in a suitable carrier or dissolved or suspended in a semi-solid formulation. Alternatively the crosslinker is encapsulated within micro- or nano-particles which are suspended in any of the above matrices or attached directly, either covalently or non-covalently to the surface of the non-absorbable patch. Also, the crosslinker could be incorporated into a biodegradable (absorbable) polymer and then used to either coat or impregnate the non-absorbable patch.

A large number of protein crosslinkers could be used in conjunction with the present invention. Some such crosslinkers that have been used in the area of tissue engineering include, but are not limited to: D- or L-Threose [63], genipin [64-67], Methylglyoxal [68], 1-ethyl-3-(3-dimethylaminopropyl) carbodiimide hydrochloride [69], proanthrocyanidin [47] and glutaraldehyde [70-72]. In particular embodiments, the crosslinker may be a single crosslinker or a combination of two or more crosslinkers. It has been shown that the conditions that confer optimal reactivity of such crosslinkers differ between reagents [58] and that in some cases other chemicals can enhance their reactivity [53]. In addition, some detergents can also enhance the penetration of crosslinkers through collagenous tissues and therefore help to enhance their ability to crosslink the tissue [53]. Thus, some embodiments may include a chemical or detergent, or any combination thereof, that enhances the crosslinking ability of the crosslinker.

As one embodiment, the application method involves a direct injection of crosslinker in a buffered reagent into the torn meniscus. The crosslinker can be selected from several known minimally toxic crosslinking agents such as genipin at a level of up to 1200 micromoles and concentration of at least 5 mM (preferably 20-100 mM) and the buffer can be 25-250 mM EPPS 4-(2-Hydroxyethyl)-1-piperazinepropanesulfonic acid (EPPS) (preferably approximately 50 mM) at a pH of 7-10 (preferably 8) and optionally contain 25-250 mM of a phosphate salt (preferably 50 mM) to facilitate the crosslinking reaction and also optionally contain a co-solvent such as dimethyl sulfoxide (at 1-50%, preferably 10-20%) to increase the solubility of the crosslinker.

In some embodiments, the crosslinker and conditioning agents are imbedded into a biodegradable meniscus fixation dart. The crosslinker can be any of several known minimally toxic crosslinking agents such as genipin or methylglyoxal at a level of about 1-10 mg per dart, though more can also be incorporated. Additionally the fixation device can also optionally contain an alkaline salt such as calcium hydroxyapatite to maintain an elevated pH as the device degrades at a level of about 5-50% by weight of the polymer (preferably about 15-30%).

In some embodiments, the crosslinker and conditioning agents are imbedded into a biodegradable suture suitable for meniscus repair using standard repair techniques. The crosslinker can be any of several known minimally toxic crosslinking agents such as genipin or methylglyoxal at a level of about 0.1-10% by weight of the polymer (preferably about 1-5%). Additionally the suture can also optionally contain an alkaline salt such as sodium bicarbonate to maintain an elevated pH as the device degrades at a level of about 5-50% by weight of the polymer (preferably about 5-15%).

In some embodiments, the crosslinker and conditioning agents are imbedded into a biodegradable meniscus repair patch. The crosslinker can be selected from any of several known minimally toxic crosslinking agents such as genipin at a level of about 1-250 mg per patch (preferably about 5-20 mg). Additionally the patch can also optionally contain an alkaline salt such as calcium carbonate to maintain an elevated pH as the device degrades at a level of about 5-50% by weight of the polymer (preferably about 15-30%). The crosslinker embedded into the patch may, therefore, be incorporated into a formulation that is designed to optimize its activity by the suitable adjustment or addition of, but not exclusively, pH, ionic strength, cations, anions, phosphate ions, and/or surfactants.

In addition, different crosslinkers can exert different mechanical effects [53]. Thus combination of crosslinkers may also be incorporated into embodiments in order to modulate the final mechanical properties of the meniscal tissue. Thus the fixation device may contain a mixture of two or more crosslinking agents.

In some embodiments the bulk of the fixation device or patch contains one or more crosslinkers that are incorporated into the device during the molding stage as described above. The device is then coated using a solvent mixture as described above but containing a different crosslinker or mixture of crosslinkers. Alternatively the device may be coated with additional layers of material by applying molten polymer containing crosslinker with or without additional agents, or a solvent-precipitated polymer gum containing crosslinker with or without additional agents.

Thus the release of different crosslinkers is controlled temporally by the order in which they are encapsulated. For example, a device might contain a crosslinker that increases tissue tear resistance but be coated with a crosslinker that preferentially increases permeability. In this manner the device will first enhance permeability of the tissue to both rapidly aid in the initiation of natural repair and prepare the tissue for ready diffusion of the second crosslinker, and only later release a crosslinker to strengthen the tissue. Alternatively, the outer layer may contain a strengthening crosslinker to provide immediate improvements in meniscal tear resistance while the crosslinker that enhances permeability is released later to help facilitate natural repair.

Referring to FIG. 1, a stylized human knee meniscus 2 with a "parrot beak" type tear 4 is depicted. Following surgical repair, a patch 6 of crosslinker-impregnated material is placed over the damaged tissue. The shaded area 8 depicts the position of the patch following attachment. The patch may additionally be attached using typical surgical fixation devices or by addition of a suitable biocompatible solvent or adhesive to the side of the patch in contact with the meniscus. Over time crosslinker will diffuse out of the patch and into the tissue, both strengthening it and facilitating the diffusion of nutrients into the damaged area by increasing the tissue permeability.

In applying the methods and devices of the current application, a patient may be a person or an animal. Further, embodiments that involve the knee meniscus may be applied to similar connective tissue structures in animals, such as the stifle joint meniscus in equines. Thus, where embodiments are described in terms of the knee meniscus, other embodiments substituting the knee meniscus with similar connective tissue structures in animals are contemplated.

The present invention may be better understood by referring to the accompanying examples, which are intended for illustration purposes only and should not in any sense be construed as limiting the scope of the invention.

EXAMPLE 1

A radial tear of a human knee meniscus may be repaired by the present methods and devices in a number of embodiments. Some embodiments involve implementation of standard arthroscopic procedures for meniscal repair using darts containing a crosslinking and a pH modulating reagent. The fixation darts are manufactured as follows. One gram of 50:50 poly-D,L-lactide-co-glycolide polymer (average molecular weight of 53 kDa) is dissolved in 6 ml of acetone and then precipitated by addition of 10 ml of pure ethanol. Two hundred mg of sodium bicarbonate and 6 mg of genipin crosslinker are added to and mixed with the precipitated polymer prior to using the mixture to mould three meniscal dart devices which are dried under vacuum to solidify the polymer and remove the solvents.

EXAMPLE 2

Some embodiments involve implementation of standard arthroscopic procedures for meniscal repair using biodegradable sutures which are produced by extruding polydioxanone in the presence of 10% (w/w) of a 40% solution of methylglyoxal.

EXAMPLE 3

Some embodiments involve direct injection into the meniscal tissue in the region of the tear a buffered crosslinking reagent. The injection may be administered using standard sterile intracapsular injection techniques and fluoroscopic, arthroscopic, or any equivalent or superior imaging technology and techniques that allow for simultaneous injections. The injected solution contains 40 mM genipin in a buffer consisting of 50 mM 3-[4-(2-Hydroxyethyl)-1-piperazinyl]propanesulfonic acid (EPPS) and 50 mM sodium triphosphate at a pH of 8.0. The patient should avoid flexion-extension or weight bearing of the knee for a period of time following the injection, approximately 1 hour, to allow for diffusion of the reagent and initial crosslink formation within the meniscal tissue, followed by a period of light movement and intermittent weight bearing to encourage further movement through the tissue of unreacted reagent and to aid in the introduction of oxygen to expedite the crosslinking reactions. A direct injection of this type can be followed immediately or at a later date with use of a crosslinker impregnated repair device such as a dart or suture. Alternatively, the direct injection of a buffered crosslinking reagent into the meniscus can follow meniscal repair using standard fixation devices or crosslinker impregnated fixation devices.

EXAMPLE 4

Some embodiments involve arthroscopic or minimally invasive delivery and fixation of a meniscal repair patch to the inferior or superior articular surface of the torn meniscus. The meniscal repair patch is prepared from 2 grams of poly lactic acid by dissolving the polymer in 12 ml of acetone and then precipitating by addition of 20 ml of pure ethanol. Six hundred mg of calcium carbonate and 20 mg of genipin crosslinker are added to and mixed with the precipitated polymer prior to molding into the final device and drying under vacuum. The patch may or may not be attached to the meniscal tissue using fixing devices such as darts, tacks or sutures which may or may not also contain crosslinking agents (for example, as in Example 1).

EXAMPLE 5

The improvement in meniscal mechanical properties including tear resistance due to the present methods and devices can be measured using human or bovine cadaveric meniscal explants and in vitro experimental methods briefly summarized here. An appropriate number of tissue specimens are included in the study according to previously documented variances in mechanical properties of the selected tissue type. According to the inventors' previously published protocol (Slusarewicz, et al., 2011, Spine, "Optimization of protein crosslinking formulations . . . " [49]), two adjacent circumferential dumbbell-shaped specimens are excised from the inner region of sixteen medial or lateral menisci for tensile testing. One specimen from each pair is treated with a crosslinking agent either via soaking in a buffered crosslinking solution such as 40 mM genipin in a buffer consisting of 50 mM 3-[4-(2-Hydroxyethyl)-1-piperazinyl]propanesulfonic acid (EPPS) and 50 mM sodium triphosphate at a pH of 8.0, or injecting approximately 0.1-0.5 ml of such a buffered crosslinking reagent using a small, greater than 20 gauge, or insulin-sized needle. Control specimens are mock-treated (soaked or injected) using the same buffer without crosslinker. Samples are subjected to strain-rate controlled tensile testing until failure using a suitable materials testing system and soft-tissue compatible clamps to hold the ends of the dumbbell-shaped specimens without tearing or damaging the specimens at the clamping site. The data is normalized using the specimen's cross-sectional area measured with a rotating laser micrometer, and the yield stress, modulus, resilience, ultimate tensile stress, and toughness are calculated. Comparisons between groups are evaluated using Wilcoxon non-parametric paired analysis. The effect of the crosslinking treatment is evidenced by a statistically significant and greater than 20% improvement in at least one of the measured mechanical properties following crosslinking treatment.

Fatigue degradation studies are conducted similarly, with the tensile tests conducted on repetitively cycled (1000 or greater numbers of pseudophysiologic cycles) or non-cycled pairs of specimens. Previous experience conducting these tests suggest that a minimum of 8-pairs of crosslinked and buffer treated specimens are required to show a statistically significant and meaningful difference in fatigue resistance. The effect of the crosslinking treatment is evidenced by a statistically significant and 30% or greater reduction in some elastic-plastic or viscoelastic property degradation due to repetitive cycling. For example, crosslinker treated meniscus specimens demonstrate a greater than 30% reduction in the increase in stress relaxation due to repetitive loading compared to the sham treated meniscus specimens.

Transverse (transverse to the long axis of the meniscus specimens) tear resistance testing is conducted in the following manner. 2 mm (axial)×8 mm (transverse) inner meniscus longitudinal (circumferential) specimens are dissected from the rear half of sixteen lateral or medial knee menisci. A transverse directed v-shaped notch defect is created with a scalpel in the mid-section of the specimen. The thickness of the specimen in the region of the defect and the distance between the tip of the defect and the edge of the specimen opposite the defect are measured using a laser non-contacting micrometer. The specimen is held taunt with its ends fixed in soft-tissue compatible clamps, while a metal cylinder is positioned in the notch defect and then pulled transversely through the specimen while force (on the pin) and displacement are recorded. A longitudinal (long axis of the meniscus specimen) tear testing protocol involves the use of sixteen front (cephalo) hemi-lateral meniscus specimens which are microtomed and dissected into ASTM style "pants legs" tear samples (12 mm×2 mm×circumferential length with a cut following the longitudinal contour leaving 8 mm uncut) for longitudinal tear testing. The thickness of the specimen in the uncut region and the distance between the "crotch" of the pants cut and the edge of the specimen opposite the cut are measured using a laser non-contacting micrometer. These material tear-propogation tests are commonly performed. Briefly, the ends of the specimen "legs" are pulled in opposite directions using a suitable materials testing system and soft-tissue compatible clamps at a constant rate of displacement while measuring applied force and displacement. Tear testing specimens are divided equally into crosslinker treated and sham treated groups. For both transverse and longitudinal tear tests, peak tear force and total energy to propagate the tear are compared between groups using Mann-Whitney non-parametric statistical tests. The effect of the crosslinking treatment is evidenced by a statistically significant and greater than 20% increase in peak force and total energy required to propagate a tear through the meniscal tissue in both transverse and longitudinal directions.

EXAMPLE 6

Improvement in meniscal cell viability following crosslinking treatment can be quantified experimentally in a number of ways. One method of quantifying this improvement is to measure the increase in tissue permeability associated with a crosslinking treatment of the present invention. Permeability is analyzed using a Franz cell system. Franz cells are glass chambers consisting of lower receptor and upper donor chambers with the sample sandwiched between them. The lower chamber is filled with a suitable buffer while the donor chamber contains a suitable small probe molecule dissolved in buffer. The permeability of the tissue governs the rate of the diffusion and presence of the probe molecule in the receptor fluid. A suitable probe molecule penetrates but doesn't bind to the tissue. Suitable probe molecules can be chromophores such as pnitrophenol or fluorophores such as fluorocein. In either case, a simple colorimetric or fluorometric (if greater sensitivity is required) assay is used to quantify the appearance of the probe in the receptor chamber. The baseline kinetics of penetration for normal meniscus is first quantified. Six (based on prior work of Hunter, et al., 2005, Journal of Orthopaedic Research [26]) tissue samples are treated with crosslinking reagent either by soaking in 40 mM genipin in a buffer consisting of 50 mM 3-[4-(2-Hydroxyethyl)-1-piperazinyl]propanesulfonic acid (EPPS) and 50 mM sodium triphosphate at a pH of 8.0, or by a direct injection of the buffered crosslinking reagent into the meniscus specimen as described in Example 5 above. An additional six controls are treated in a similar manner with buffer alone. Samples are then cut to the same thickness using a microtome. Kinetic analysis is conducted by periodically sampling and analyzing the receptor fluid, facilitating quantitative determination of tissue permeability. The effect of the crosslinking treatment suggesting improved cell viability in this largely avascular tissue is evidenced by a statistically significant and greater than 40% increase in tissue permeability.

REFERENCES

The following publications are incorporated by reference herein:
1. Allen P R, Denham R A, Swan A V. Late degenerative changes after meniscectomy. Factors affecting the knee after operation. *J. Bone Joint Surg. Br.* 1984; 66:666-71.
2. Fairbank T J. Knee joint changes after meniscectomy. *J. Bone Joint Surg. Am.* 1948; 30B:664-70.
3. Jorgensen U, Sonne-Holm S, Lauridsen F et al. Long-term follow-up of meniscectomy in athletes. A prospective longitudinal study. *J. Bone Joint Surg. Br.* 1987; 69:80-3.
4. Walker P S, Erkman M J. The role of the menisci in force transmission across the knee. *Clin. Orthop. Relat Res.* 1975; 184-92.
5. Fu F H, Thompson W O. Motion of the knee meniscus during knee flexion. In: Mow V C, Arnoczky S P, Jackson D W, eds. *Knee Meniscus: Basic and Clinical Foundations*. New York, N.Y.: Raven Press, 1992:75-89.
6. Levy I M, Torzilli P A, Fisch I D. The contribution of the menisci to the stability of the knee. In: Mow V C, Arnoczky S P, Jackson D W, eds. *Knee Meniscus: Basic and Clinical Foundations*. New York, N.Y.: Raven Press, 1992:107-15.
7. Proctor C S, Schmidt M B, Whipple R R et al. Material properties of the normal medial bovine meniscus. *J. Orthop. Res.* 1989; 7:771-82.
8. Arendt E A. *Orthopaedic Knowledge Update: Sports Medicine* 2. Rosemont, Ill.: American Academy of Orthopaedic Surgeons, 1999.
9. Jakob R P, Staubli H U, Zuber K et al. The arthroscopic meniscal repair. Techniques and clinical experience. *Am. J. Sports Med.* 1988; 16:137-42.
10. Rosenberg T D, Scott S M, Coward D B et al. Arthroscopic meniscal repair evaluated with repeat arthroscopy. *Arthroscopy* 1986; 2:14-20.
11. Hennerbichler A, Moutos F T, Hennerbichler D et al. Repair response of the inner and outer regions of the porcine meniscus in vitro. *Am. J. Sports Med.* 2007; 35:754-62.
12. Barber F A, Herbert M A, Richards D P. Load to failure testing of new meniscal repair devices. *Arthroscopy* 2004; 20:45-50.
13. Barber F A, Herbert M A. Meniscal repair devices. *Arthroscopy* 2000; 16:613-8.
14. Rankin C C, Lintner D M, Noble P C et al. A biomechanical analysis of meniscal repair techniques. *Am. J. Sports Med.* 2002; 30:492-7.
15. Izuta Y, Ochi M, Adachi N et al. Meniscal repair using bone marrow-derived mesenchymal stem cells: experimental study using green fluorescent protein transgenic rats. *Knee.* 2005; 12:217-23.
16. Yamasaki T, Deie M, Shinomiya R et al. Meniscal regeneration using tissue engineering with a scaffold derived from a rat meniscus and mesenchymal stromal cells derived from rat bone marrow. *J. Biomed. Mater. Res. A* 2005; 75:23-30.
17. Zhang Z, Arnold J A. Trephination and suturing of avascular meniscal tears: a clinical study of the trephination procedure. *Arthroscopy* 1996; 12:726-31.
18. Fox J M, Rintz K G, Ferkel R D. Trephination of incomplete meniscal tears. *Arthroscopy* 1993; 9:451-5.
19. Cook J L, Fox D B. A novel bioabsorbable conduit augments healing of avascular meniscal tears in a dog model. *Am. J. Sports Med.* 2007; 35:1877-87.
20. Freedman K B, Nho S J, Cole B J. Marrow stimulating technique to augment meniscus repair. *Arthroscopy* 2003; 19:794-8.
21. Imakiire N, Kotani A, Ishii Y. Experimental study on thermal welding for the knee meniscal white zone. *J. Orthop. Sci.* 2003; 8:683-92.
22. Hatayama K, Higuchi H, Kimura M et al. Histologic changes after meniscal repair using radiofrequency energy in rabbits. *Arthroscopy* 2007; 23:299-304.
23. Lopez M J, DeTemple L A, Lu Y et al. The effects of monopolar radiofrequency energy on intact and lacerated ovine menisci. *Arthroscopy* 2001; 17:613-9.
24. Arnoczky S P, Warren R F, Spivak J M. Meniscal repair using an exogenous fibrin clot. An experimental study in dogs. *J. Bone Joint Surg. Am.* 1988; 70:1209-17.
25. Sethi P M, Cooper A, Jokl P. Technical tips in orthopaedics: meniscal repair with use of an in situ fibrin clot. *Arthroscopy* 2003; 19:E44.
26. van Trommel M F, Simonian P T, Potter H G et al. Arthroscopic meniscal repair with fibrin clot of complete radial tears of the lateral meniscus in the avascular zone. *Arthroscopy* 1998; 14:360-5.
27. Forman S K, Oz M C, Lontz J F et al. Laser-assisted fibrin clot soldering of human menisci. *Clin. Orthop. Relat Res.* 1995; 37-41.
28. Ochi M, Uchio Y, Okuda K et al. Expression of cytokines after meniscal rasping to promote meniscal healing. *Arthroscopy* 2001; 17:724-31.
29. Okuda K, Ochi M, Shu N et al. Meniscal rasping for repair of meniscal tear in the avascular zone. *Arthroscopy* 1999; 15:281-6.
30. Talley M C, Grana W A. Treatment of partial meniscal tears identified during anterior cruciate ligament reconstruction with limited synovial abrasion. *Arthroscopy* 2000; 16:6-10.
31. Nakhostine M, Gershuni D H, Anderson R et al. Effects of abrasion therapy on tears in the avascular region of sheep menisci. *Arthroscopy* 1990; 6:280-7.
32. Jitsuiki J, Ochi M, Ikuta Y. Meniscal repair enhanced by an interpositional free synovial autograft: an experimental study in rabbits. *Arthroscopy* 1994; 10:659-66.

33. Tienen T G, Heijkants R G, de Groot J H et al. Replacement of the knee meniscus by a porous polymer implant: a study in dogs. *Am. J. Sports Med.* 2006; 34:64-71.
34. Stone K R, Steadman J R, Rodkey W G et al. Regeneration of meniscal cartilage with use of a collagen scaffold. Analysis of preliminary data. *J. Bone Joint Surg. Am.* 1997; 79:1770-7.
35. Stone K R, Rodkey W G, McKinney L A et al. Autogenous replacement of the meniscus cartilage: analysis of results and mechanisms of failure. *Arthroscopy* 1995; 11:395-400.
36. Stone K R, Rodkey W G, Webber R et al. Meniscal regeneration with copolymeric collagen scaffolds. In vitro and in vivo studies evaluated clinically, histologically, and biochemically. *Am. J. Sports Med.* 1992; 20:104-11.
37. Stone K R, Rodkey W G, Webber R J et al. Future directions. Collagen-based prostheses for meniscal regeneration. *Clin. Orthop. Relat Res.* 1990; 129-35.
38. Milachowski K A, Weismeier K, Wirth C J. Homologous meniscus transplantation. Experimental and clinical results. *Int. Orthop.* 1989; 13:1-11.
39. Garrett J C, Steensen R N. Meniscal transplantation in the human knee: a preliminary report. *Arthroscopy* 1991; 7:57-62.
40. Arnoczky S P, Warren R F, McDevitt C A. Meniscal replacement using a cryopreserved allograft. An experimental study in the dog. *Clin. Orthop. Relat Res.* 1990; 121-8.
41. Hunter S A, Noyes F R, Haridas B et al. Meniscal material properties are minimally affected by matrix stabilization using glutaraldehyde and glycation with ribose. *J. Orthop. Res.* 2005; 23:555-61.
42. Stone K R. Prosthetic meniscus. ReGen Corporation. (U.S. Pat. No. 5,007,934). 3-2-0989.
43. Wisnewski P J, Powers D L, Kennedy J M. Glutaraldehyde-cross-linked meniscal allografts: mechanical properties. *J. Invest Surg.* 1988; 1:259-66.
44. Powers D L, Davenport M E, Wisnewski P J. Glutaraldehyde-cross-linked meniscal allografts: clinical, gross, and histological results. *J. Invest Surg.* 1988; 1:249-57.
45. Charulatha V, Rajaram A. Influence of different cross-linking treatments on the physical properties of collagen membranes. *Biomaterials* 2003; 24:759-67.
46. Chuang S Y, Odono R M, Hedman T P. Effects of exogenous crosslinking on in vitro tensile and compressive moduli of lumbar intervertebral discs. *Clin. Biomech.* 2007; 22:14-20.
47. Han B, Jaurequi J, Tang B W et al. Proanthocyanidin: a natural crosslinking reagent for stabilizing collagen matrices. *J. Biomed. Mater. Res. A* 2003; 65:118-24.
48. Slusarewicz P, Zhu K, Hedman T P. Kinetic Characterization and Comparison of Various Protein Crosslinking Reagents for Matrix Modification. *J. Mater. Sci. Mater. Med.* 2010; DOI: 10.1007/s10856-010-3986-8.
49. Sung H W, Liang I L, Chen C N et al. Stability of a biological tissue fixed with a naturally occurring crosslinking agent (genipin). *J. Biomed. Mater. Res.* 2001; 55:538-46.
50. Tang S Y, Sharan A D, Vashishth D. Effects of collagen crosslinking on tissue fragility. *Clin. Biomech.* (Bristol., Avon.) 2008; 23:122-3.
51. Vasudev S C, Chandy T. Effect of alternative crosslinking techniques on the enzymatic degradation of bovine pericardia and their calcification. *J. Biomed. Mater. Res.* 1997; 35:357-69.
52. Zhai W, Chang J, Lin K et al. Crosslinking of decellularized porcine heart valve matrix by procyanidins. *Biomaterials* 2006; 27:3684-90.
53. Slusarewicz P, Zhu K, Kirking B et al. Optimization of Protein Crosslinking Formulations for the Treatment of Degenerative Disc Disease. *Spine* 2010; In Press.
54. Boyd-White J, Williams J C, Jr. Effect of cross-linking on matrix permeability. A model for AGE-modified basement membranes. *Diabetes* 1996; 45:348-53.
55. Chuang S Y, Popovich J M, Lin L C et al. The Effects of Exogenous Crosslinking on Hydration and Fluid Flow in the Intervertebral Disc Subjected to Compressive Creep Loading and Unloading. *Submitted to Spine* 2009.
56. Athanasiou K A, Singhal A R, Agrawal C M et al. In vitro degradation and release characteristics of biodegradable implants containing trypsin inhibitor. *Clin. Orthop. Relat Res.* 1995; 272-81.
57. Singhal A R, Agrawal C M, Athanasiou K A. Salient Degradation Features of a 50:50 PLA/PGA Scaffold for Tissue Engineering. *Tissue Eng* 1996; 2:197-207.
58. Slusarewicz P, Zhu K, Hedman T. Kinetic characterization and comparison of various protein crosslinking reagents for matrix modification. *J. Mater. Sci. Mater. Med.* 2010; 21:1175-81.
59. Agrawal C M, Athanasiou K A. Technique to control pH in vicinity of biodegrading PLA-PGA implants. *J. Biomed. Mater. Res.* 1997; 38:105-14.
60. Mandavi A, Ferreira L, Sundback C et al. A biodegradable and biocompatible gecko-inspired tissue adhesive. *Proc. Natl. Acad. Sci. U.S.A* 2008; 105:2307-12.
61. Klapperich C M, Noack C L, Kaufman J D et al. A novel biocompatible adhesive incorporating plant-derived monomers. *J. Biomed. Mater. Res. A* 2009; 91:378-84.
62. Jonn J Y, Bobo J, Quintero J et al. Absorbable adhesive compositions. (U.S. Pat. No. 6,620,846). 2000. US.
63. Verzijl N, De Groot J, Ben Z C et al. Crosslinking by advanced glycation end products increases the stiffness of the collagen network in human articular cartilage: a possible mechanism through which age is a risk factor for osteoarthritis. *Arthritis Rheum.* 2002; 46:114-23.
64. Sung H W, Chang Y, Chiu C T et al. Crosslinking characteristics and mechanical properties of a bovine pericardium fixed with a naturally occurring crosslinking agent. *J. Biomed. Mater. Res.* 1999; 47:116-26.
65. Sung H W, Chang Y, Chiu C T et al. Mechanical properties of a porcine aortic valve fixed with a naturally occurring crosslinking agent. *Biomaterials* 1999; 20:1759-72.
66. Hedman T P, Saito H, Vo C et al. Exogenous crosslinking increases the stability of spinal motion segments. *Spine* 2006; 31:480-5.
67. Yerramalli C S, Chou A I, Miller G J et al. The effect of nucleus pulposus crosslinking and glycosaminoglycan degradation on disc mechanical function. *Biomech. Model. Mechanobiol.* 2007; 6:13-20.
68. Wagner D R, Reiser K M, Lotz J C. Glycation increases human annulus fibrosus stiffness in both experimental measurements and theoretical predictions. *J. Biomech.* 2006; 39:1021-9.
69. Gratzer P F, Lee J M. Control of pH alters the type of cross-linking produced by 1-ethyl-3-(3-dimethylaminopropyl)-carbodiimide (EDC) treatment of acellular matrix vascular grafts. *J. Biomed. Mater. Res.* 2001; 58:172-9.
70. Wu X, Black L, Santacana-Laffitte G et al. Preparation and assessment of glutaraldehyde-crosslinked collagen-chitosan hydrogels for adipose tissue engineering. *J. Biomed. Mater. Res. A* 2007; 81:59-65.

71. Yang S H, Hsu C K, Wang K C et al. Tricalcium phosphate and glutaraldehyde crosslinked gelatin incorporating bone morphogenetic protein—a viable scaffold for bone tissue engineering. *J. Biomed. Mater. Res. B Appl. Biomater.* 2005; 74:468-75.
72. Hoffmann B, Seitz D, Mencke A et al. Glutaraldehyde and oxidised dextran as crosslinker reagents for chitosan-based scaffolds for cartilage tissue engineering. *J. Mater. Sci. Mater. Med.* 2009; 20:1495-503.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A method of treating a tear in a knee meniscus of a patient, comprising contacting a torn knee meniscus with a delivery device comprising a protein crosslinking agent during surgery to repair the tear, wherein the crosslinking agent increases the number of covalent crosslink bonds between native tissue proteins in the knee meniscus.

2. The method of claim 1, wherein the delivery device comprises a patch or fixation device comprising the crosslinking agent.

3. The method of claim 2, wherein the fixation device is an arrow, dart, tack or suture.

4. The method of claim 2, wherein the patch or fixation device is biodegradable.

5. The method of claim 2, wherein the patch or fixation device further comprises a basic salt.

6. The method of claim 5, wherein the basic salt is calcium carbonate, calcium hydroxyapatite, sodium bicarbonate, 2-Amino-2-hydroxymethyl-propane-1,3-diol (Tris) or 4-(2-hydroxyethyl)-1-piperazineethanesulfonic acid (HEPES).

7. The method of claim 2, wherein the patch is non-biodegradable.

8. The method of claim 2, wherein the patch is porous and the crosslinking agent is embedded within the pores.

9. The method of claim 2, wherein the crosslinking agent is adhered to one side of the patch as part of a semi-solid formulation.

10. The method of claim 2, wherein the patch or fixation device is coated with one or more layers of crosslinking agent-containing biodegradable polymer.

11. The method of claim 10, wherein each layer comprises a basic salt.

12. The method of claim 11, wherein the salt is calcium carbonate, calcium hydroxyapatite, sodium bicarbonate, 2-Amino-2-hydroxymethyl-propane-1,3-diol (Tris) or 4-(2-hydroxyethyl)-1-piperazineethanesulfonic acid (HEPES).

13. The method of claim 10, wherein the patch or fixation device is coated with multiple layers of crosslinking agent-containing biodegradable polymer, and the crosslinking agent varies from layer to layer.

14. The method of claim 2, wherein the patch is affixed to the meniscus with a bio-compatible adhesive.

15. The method of claim 14, wherein the adhesive is poly(glycerol-co-sebacate acrylate), an oleic methyl ester or an alkyl ester cyanoacrylate.

16. The method of claim 2, wherein the patch is affixed to the meniscus by an associated fixation device.

17. The method of claim 16, wherein the associated fixation device is an arrow, dart, tack or suture.

18. The method of claim 16, wherein the associated fixation device comprises a crosslinking agent.

19. The method of claim 1, wherein the protein crosslinking agent is genipin, D- or L-threose, methylglyoxal, 1-ethyl-3-(3-dimethylaminopropyl) carbodiimide hydrochloride, proanthrocyanidin, or glutaraldehyde.

20. The method of claim 13, wherein the crosslinking agent comprises any combination of two or more compounds selected from the group consisting of genipin, D- or L-threose, methylglyoxal, 1-ethyl-3-(3-dimethylaminopropyl) carbodiimide hydrochloride, proanthrocyanidin, and glutaraldehyde.

21. The method of claim 2, wherein the fixation device contains about 1 to 10 mg of genipin or methylglyoxal.

22. The method of claim 2, wherein the patch contains genipin at a level of about 1 to 250 mg.

23. The method of claim 4, wherein the patch or fixation device contains genipin or methylglyoxal at a level of about 0.1 to 10% by weight of the polymer.

24. The method of claim 10, wherein the one or more layers contain genipin or methylglyoxal at a level of about 0.1 to 10% by weight of the polymer.

* * * * *